United States Patent
Ko et al.

(10) Patent No.: US 12,235,583 B2
(45) Date of Patent: Feb. 25, 2025

(54) MICROPATTERNING METHOD, MICROPATTERNING APPARATUS AND MICROPATTERNING CHIP FOR SILICONE-BASED ELASTOMER

(71) Applicant: SEOUL NATIONAL UNIVERSITY R&DB FOUNDATION, Seoul (KR)

(72) Inventors: Seung Hwan Ko, Seoul (KR); Jae Ho Shin, Incheon (KR); Phil Lip Won, Seoul (KR); Seong Min Jeong, Seoul (KR)

(73) Assignee: SEOUL NATIONAL UNIVERSITY R&DB FOUNDATION, Seoul (KR)

( * ) Notice: Subject to any disclaimer, the term of this patent is extended or adjusted under 35 U.S.C. 154(b) by 563 days.

(21) Appl. No.: 17/762,227

(22) PCT Filed: Apr. 10, 2020

(86) PCT No.: PCT/KR2020/004868
§ 371 (c)(1),
(2) Date: Mar. 21, 2022

(87) PCT Pub. No.: WO2020/218763
PCT Pub. Date: Oct. 29, 2020

(65) Prior Publication Data
US 2022/0350250 A1    Nov. 3, 2022

(30) Foreign Application Priority Data

Apr. 26, 2019  (KR) .................. 10-2019-0049369
Mar. 27, 2020  (KR) .................. 10-2020-0037522

(51) Int. Cl.
*G03F 7/20*       (2006.01)
*B29C 59/16*      (2006.01)
*B29K 83/00*      (2006.01)
*B81B 1/00*       (2006.01)
*B81C 1/00*       (2006.01)

(52) U.S. Cl.
CPC ............ *G03F 7/2053* (2013.01); *B29C 59/16* (2013.01); *B81B 1/002* (2013.01);
(Continued)

(58) Field of Classification Search
CPC . G03F 7/2053; G03F 7/0037; B81C 1/00119; B81C 2201/0143;
(Continued)

(56) References Cited

U.S. PATENT DOCUMENTS

2005/0232116 A1* 10/2005 Misawa ............... G02B 27/144
                                                      369/103

FOREIGN PATENT DOCUMENTS

JP          3012926 B1 *  2/2000  ......... B23K 26/0624
JP       2005-156999 A     6/2005
(Continued)

OTHER PUBLICATIONS

English translation of KR-20160066739-A by EPO. (Year: 2016).*
(Continued)

*Primary Examiner* — Timothy Kennedy
*Assistant Examiner* — Inja Song
(74) *Attorney, Agent, or Firm* — Sughrue Mion, PLLC

(57) ABSTRACT

The present disclosure relates to a method for micropatterning on silicone-based elastomer, the method including forming an initiator at a position of the silicone-based elastomer having high optical transmittance and transparency, and moving a laser beam to induce chain pyrolysis, thereby forming micropatterns with high quality in a very short time.

10 Claims, 17 Drawing Sheets

(52) U.S. Cl.
CPC ...... *B81C 1/00119* (2013.01); *B29K 2083/00* (2013.01); *B81B 2201/05* (2013.01); *B81C 2201/0143* (2013.01)

(58) Field of Classification Search
CPC ..... B29K 2083/00; B29C 59/16; B81B 1/002; B81B 2201/05; B33Y 10/00; B33Y 70/00; C08J 2383/04; C08J 7/123; C12M 23/16; C12M 23/20; C12M 23/22; B23K 26/082; B23K 26/0853; B23K 26/0608; B23K 2103/42
See application file for complete search history.

(56) References Cited

FOREIGN PATENT DOCUMENTS

| JP | 2008-507114 A | | 3/2008 |
|---|---|---|---|
| JP | 2013-116504 A | | 6/2013 |
| JP | 2014226685 A | * | 12/2014 |
| JP | 2018-114544 A | | 7/2018 |
| KR | 10-2016-0066739 A | | 6/2016 |

OTHER PUBLICATIONS

English translation of JP-2005156999-A by EPO. (Year: 2005).*
English translation of JP-2014226685-A. (Year: 2014).*
English translation of JP-3012926-B1. (Year: 2000).*
Jaeho Shin, et al., "Monolithic digital patterning of polydimethylsiloxane with successive laser pyrolysis", Nature Materials, Jan. 2021, pp. 100-107, vol. 20.
International Search Report for PCT/KR2020/004868 dated Jul. 27, 2020 (PCT/ISA/210).
Written Opinion for PCT/KR2020/004868 dated Jul. 27, 2020 (PCT/ISA/237).

* cited by examiner

FIG. 5
(a) Front Surface Scanning (FSS)
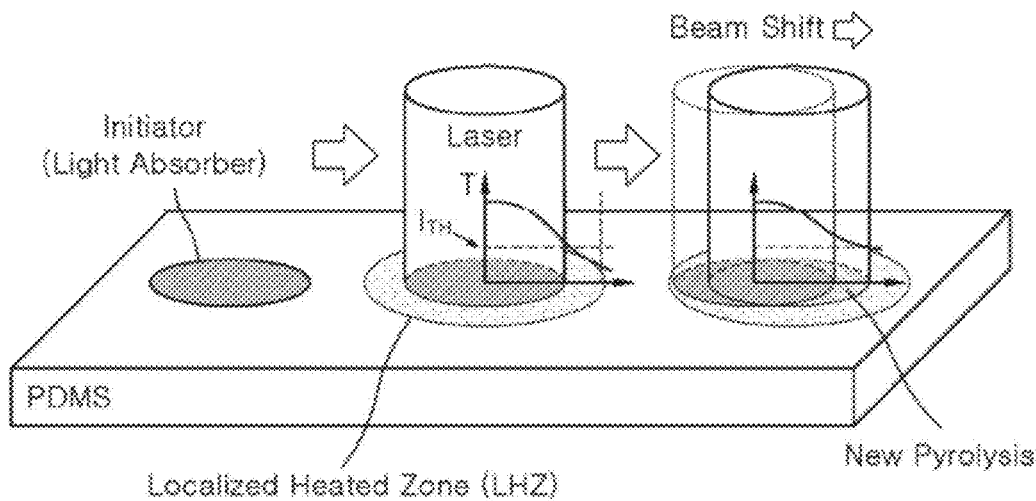
(b) Back Surface Scanning (BSS)
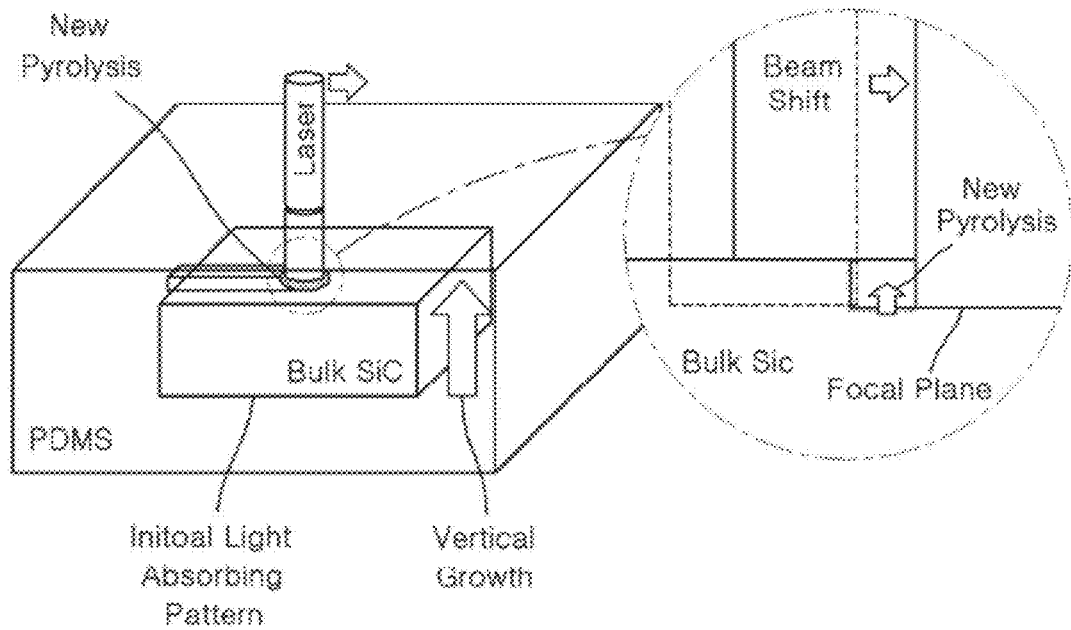

FIG. 9
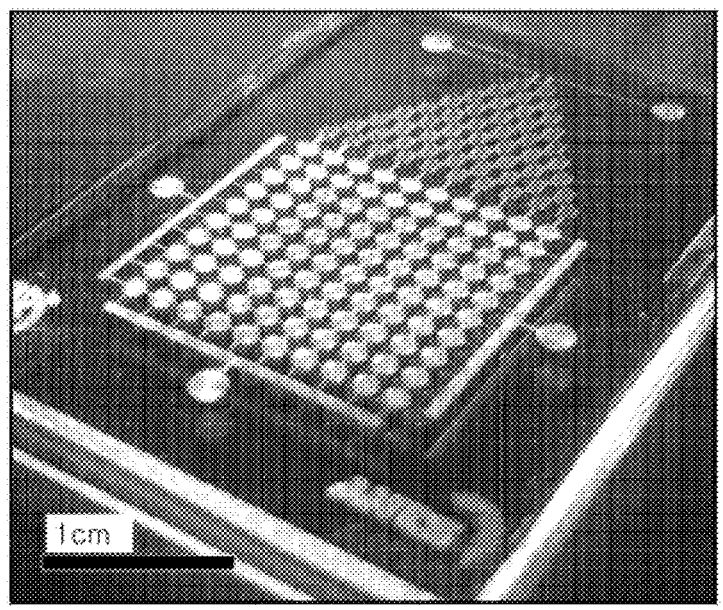
(a)
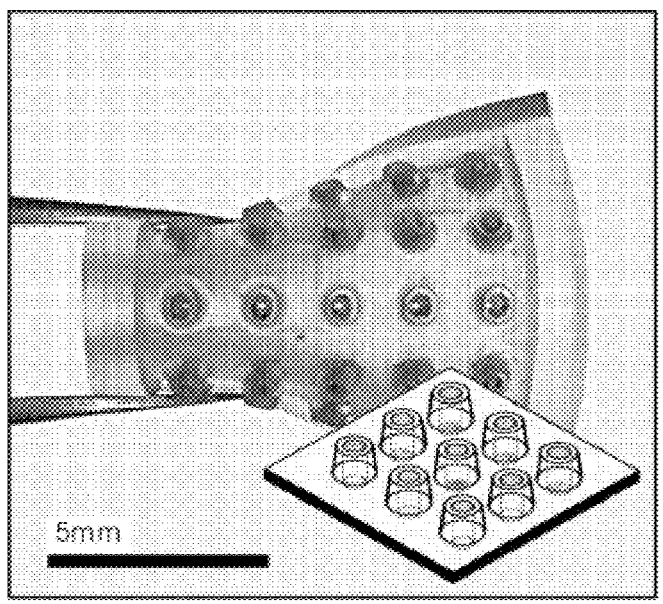
(b)

FIG. 12
(a)
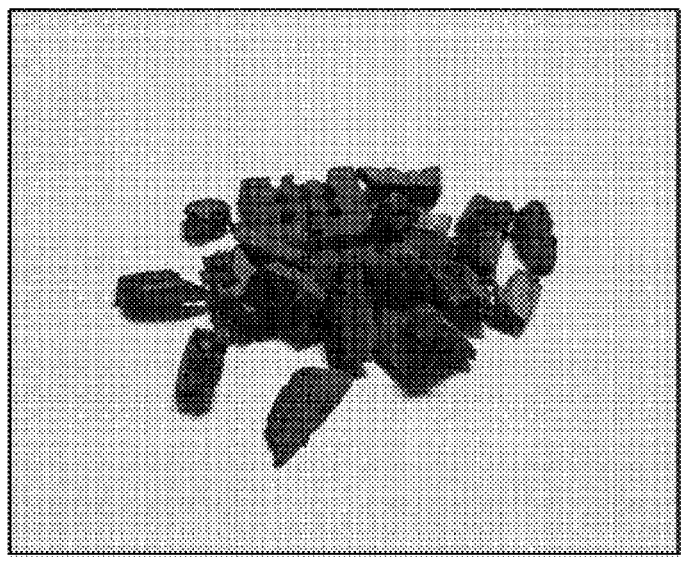
(b)
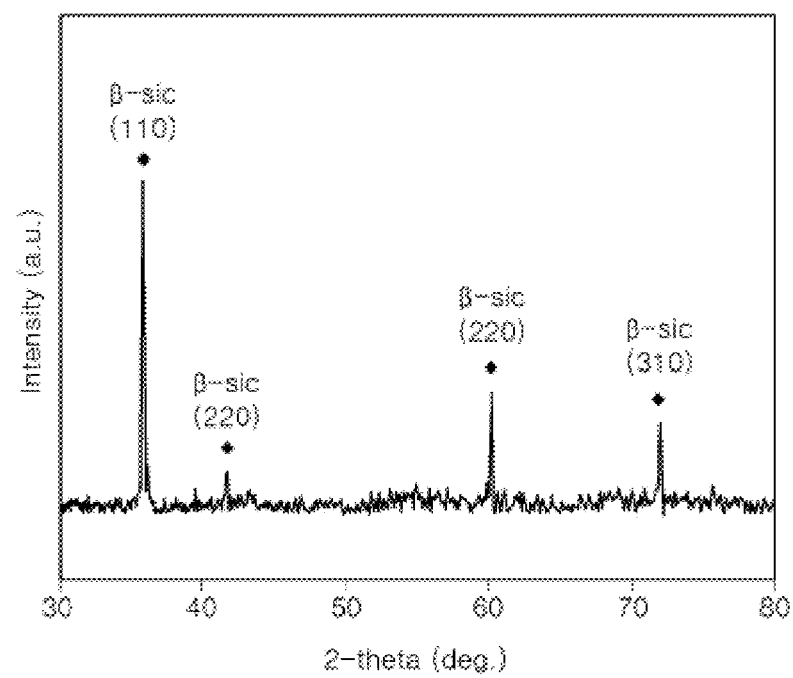

FIG. 15
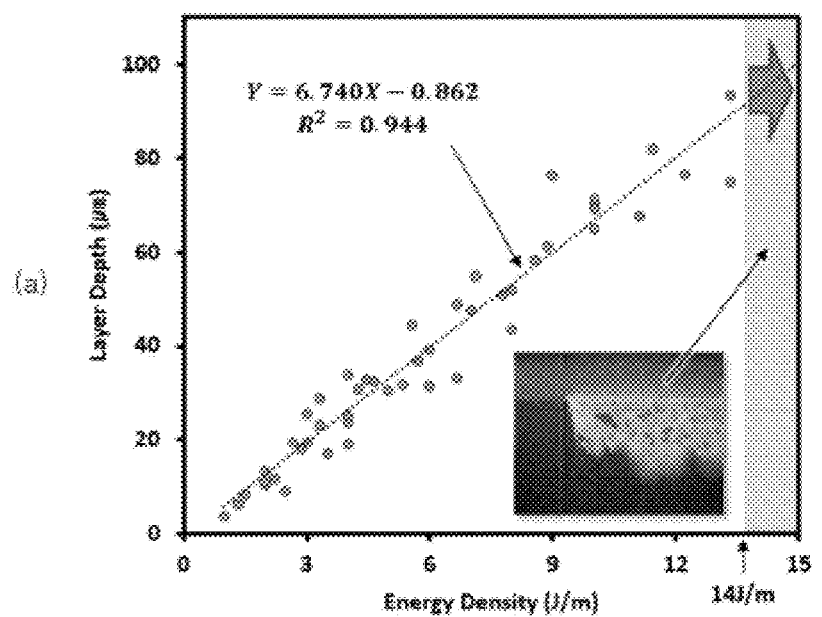
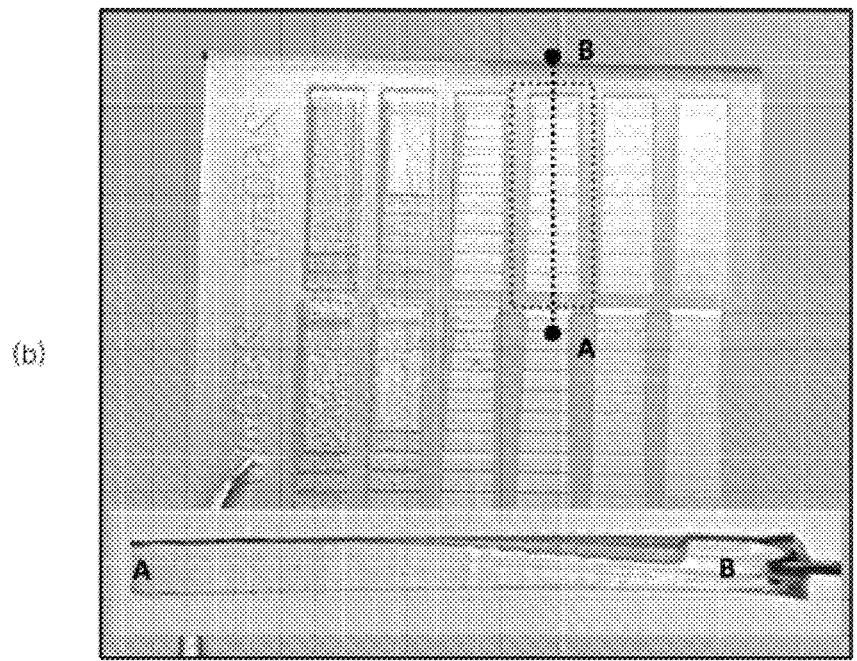

FIG. 17

| Categories | Type 1 Gradient Generator | Type 2 Perfusable Cell-bed | Type 3 Vascular-on-a-chip | Type 4 High AR Pillar Array |
|---|---|---|---|---|
| Overall Image | | | | |
| Highlighted Image | | | | |
| | FSS, Monotonic, Linear, Single-layer | FSS, Gray Scale, Semi-areal, Single-layer | BSS, Monotonic, Areal, Multi-layer | BSS, Monotonic, Areal, Multi-layer |
| Pattern Density/ Size/ Lead Time | 10 mm/cm² 12 cm² 40 s/EA | 30 mm/cm² 12 cm² 2 min/EA | 200 mm/cm² 6 cm² 7 min/EA | 20 mm/cm² 1 cm² 1 min/EA |
| Requirement | Unicursal Scanning | Unicursal Scanning | Outilne adjustment | Adaptive stage control (z-axis) |
| Mass Production | ●●●●● | ●●●●○ | ●●●○○ | ●●●●○ |

Legend: FSS, BSS, Monotone, Gray Scale, Linear Pattern, Areal Pattern, Monolayer, Multi-layer Front Surface Scanning
Back Surface Scanning < 1min/EA    1~3min/EA
3~5min/EA    > 5min/EA

MICROPATTERNING METHOD, MICROPATTERNING APPARATUS AND MICROPATTERNING CHIP FOR SILICONE-BASED ELASTOMER

CROSS REFERENCE TO RELATED APPLICATIONS

This application is a National Stage of International Application No. PCT/KR2020/004868 filed Apr. 10, 2020, claiming priorities based on Korean Patent Application No. 10-2019-0049369 filed Apr. 26, 2019 and Korean Patent Application No. 10-2020-0037522 filed Mar. 27, 2020, the entire disclosures of which are incorporated herein by reference.

TECHNICAL FIELD

The present disclosure relates to a method for micropatterning on silicone-based elastomers, and more particularly, to a method for forming precise micropatterns on transparent silicone-based elastomers using a laser.

BACKGROUND ART

Silicone-based elastomers are highly biocompatible, and thus can be used in cell culture applications, and in particular, their transparency makes it possible to observe cell growth and division in real time. Accordingly, various studies are being conducted to fabricate micropatterned chips such as biochips or organ-on-chips through micropatterning on silicone-based elastomers, for example, polydimethylsiloxane (PDMS).

In general, a photolithography process is used for micropatterning on silicone-based elastomers. However, the photolithography process is very complicated and requires expensive equipment, and in particular, needs to make a mask for each pattern to form. The photolithography mask requires high cost and long time to make.

Compared to the photolithography process, methods using a laser require a short time to perform the micropatterning process and are straightforward. However, since silicone-based elastomers having high optical transmittance and transparency allow the laser to pass therethrough, it is not easy to perform micropatterning using the laser.

Due to this problem, the conventional methods for micropatterning on silicone-based elastomers using a laser largely include the following two methods.

The first method is a method for surface ablation of silicone-based elastomers using high energy pulsed laser. However, this ablation process forms micropatterns with too low quality to be actually commercialized. FIG. 1 shows that the micropatterns formed using pulsed laser are non-uniform and uneven. It is the limitation of the pulsed laser using high energy.

The second method is a method which forms a light-absorbing layer on the surface of silicone-based elastomer, performs micropatterning using a laser, and removes the light-absorbing layer as disclosed by Journal of Micromechanics and Microengineering, 26 (2016) 035008 (8pp), Ziya Isiksacan et al., Rapid fabrication of microfluidic PDMS devices from reusable PDMS molds using laser ablation. However, the surface characteristics of the silicone-based elastomer degrade due to problems with an adhesive or a hydrophobic surface in the process of forming the light-absorbing layer on the silicone-based elastomer. For example, the low transparency or the hydrophobic surface makes it difficult to use in microfluidic device applications. Additionally, since the method for forming the light-absorbing layer uses a very complicated process and has very low efficiency in time and cost, in fact, mass production is impossible.

In these circumstances, the inventors have developed a new approach for micropatterning using a laser without degradation in the surface characteristics of transparent silicone-based elastomers.

DISCLOSURE

Technical Problem

The present disclosure is directed to providing a method for micropatterning on silicone-based elastomer with high quality in a very short time using laser-induced chain pyrolysis.

The present disclosure is further directed to providing a method for micropatterning on silicone-based elastomer for forming 3-dimensional micropatterns using laser-induced chain pyrolysis and a laser micropatterning apparatus.

The present disclosure is further directed to providing micropatterned microfluidic chips or cell culture chips fabricated through chain pyrolysis using a laser.

Another object of the present disclosure not described herein will be further considered within the readily inferable range from the following detailed description and the effects.

Technical Solution

To achieve the above-described object, a method for micropatterning on silicone-based elastomer according to an embodiment of the present disclosure includes forming a light-absorbing pyrolytic initiator having a first area at a position of the silicone-based elastomer; emitting a laser beam from a micropatterning apparatus which emits the laser beam to the pyrolytic initiator to induce first pyrolysis in the first area, wherein second pyrolysis occurs outside of the first area by conduction of heat generated by the first pyrolysis to form a second area in which light can be absorbed; and emitting the laser beam while moving the laser beam to the second area to form a micropattern.

In an embodiment, the silicone-based elastomer may have a first surface on which the laser beam is incident and a second surface opposite the first surface, and the initiator may be formed on the first surface of the silicone-based elastomer and may form a 2-dimensional (2D) micropattern with the movement of the laser beam in a 2D area.

In an embodiment, the silicone-based elastomer may have a first surface on which the laser beam is incident and a second surface opposite the first surface, and the initiator may be formed on the second surface of the silicone-based elastomer and may form a 3D micropattern with the movement of the laser beam in a 3D area.

In an embodiment, the micropatterning apparatus may generate a first axis laser beam, a second axis laser beam and a third axis laser beam, the first axis laser beam, the second axis laser beam and the third axis laser beam may intersect at a point to form an intersection point, and a 3D micropattern may be formed with movement of the intersection point in a 3D area starting from the initiator at said location of the silicone-based elastomer.

In an embodiment, the initiator may be a solution or a solid having higher light absorption than the silicone-based elastomer. For example, the initiator may be a light-absorbing color pigment, dye, ink or a solution or a solid including at least one of them.

In an embodiment, the initiator may be disposed on a surface of the silicone-based elastomer or inserted or embedded in the silicone-based elastomer.

In an embodiment, pyrolysis products may be removed after forming the micropattern. In this instance, the pyrolysis products may be SiC, SiOC, $SiO_2$, or amorphous silica.

In an embodiment, the silicone-based elastomer may be Polydimethylsiloxane.

In an embodiment, the laser beam may be a continuous-wave laser beam or a pulse laser beam.

In an embodiment, a power density of the laser beam may be less than a power density for ablation of the silicone-based elastomer.

To achieve the above-described object, a micropatterned chip of another embodiment of the present disclosure is fabricated by the above-described method for micropatterning on silicone-based elastomer, and the formed micropattern has turbidity of 4% T or more at 550 nm light.

To achieve the above-described object, a micropatterning apparatus of still another embodiment of the present disclosure includes a laser beam generation unit, a stage and a control unit to control the laser beam generation unit or the stage, and is configured to form a micropattern on silicone-based elastomer by inducing chain pyrolysis. In this instance, the laser beam generation unit includes a laser oscillator; a mirror; a beam expander; and a laser beam scanner, the silicone-based elastomer is mounted on the stage, the micropattern is formed on the silicone-based elastomer by the laser beam, and the silicone-based elastomer includes at least one initiator which absorbs light, and either the laser beam scanner or the stage or both is moved to a 2D area or a 3D area by a driving device.

In another embodiment, the laser beam generation unit may include a first laser beam generation unit to generate a first axis laser beam, a second laser beam generation unit to generate a second axis laser beam and a third laser beam generation unit to generate a third axis laser beam, and the first to third laser beam generation units may be configured to have an intersection point where the first axis laser beam, the second axis laser beam and the third axis laser beam intersect at a point.

In another embodiment, the laser beam scanner may be a galvanometer scanner.

In another embodiment, a wavelength of the laser beam generated by the laser beam generation unit may be 200 nm to 1,000 nm.

In another embodiment, a power density of the laser beam generated by the laser beam generation unit may be 10 to 100 J/m.

ADVANTAGEOUS EFFECTS

The method for micropatterning on silicone-based elastomer according to an embodiment of the present disclosure forms micropatterns with high quality in a very short time by forming an initiator at a position of the silicone-based elastomer having high optical transmittance and transparency and moving a laser beam to induce chain pyrolysis.

The laser micropatterning apparatus according to another embodiment of the present disclosure is configured to have an intersection point where the first axis laser beam, the second axis laser beam and the third axis laser beam intersect at a point, and can form 3D micropatterns through chain pyrolysis by moving the intersection point in 3 dimensions (3D) from the initiator at said position of the silicone-based elastomer.

The micropatterned chip according to still another embodiment of the present disclosure can provide micropatterned microfluidic chips, cell culture chips or organoids fabricated through chain pyrolysis using a laser beam.

Meanwhile, it is noted that although not mentioned herein, the effects described in the following description, expected by the technical features of the present disclosure and its potential effects are regarded as equal to those in the detailed description of the present disclosure.

DESCRIPTION OF DRAWINGS

FIG. 5 is a schematic diagram of a process of forming micropattern on silicon-based elastomer through chain pyrolysis according to a micropatterning method of the present disclosure.

FIGS. 8 and 9 are photographic images of a PDMS micropatterned chip on which micropatterns are formed using chain pyrolysis induced by laser beam irradiation according to a micropatterning method of the present disclosure.

FIG. 12 shows the X-ray diffraction (XRD) analysis results of pyrolysis products removed by the method of FIG. 11.

FIG. 15 is a graph showing a correlation between the power density of a laser beam and the channel layer depth of micropattern formed according to the present disclosure.

FIG. 17 shows a table of various embodiments of micropatterned chips fabricated according to the present disclosure.

It is noted that the accompanying drawings are provided for illustrative purposes to help the understanding of the technical spirit of the present disclosure, and the scope of protection of the present disclosure is not limited thereby.

BEST MODE

Hereinafter, the subject matter of the present disclosure guided by various embodiments of the present disclosure and effects resulting from the subject matter will be described with reference to the accompanying drawings. In the description of the present disclosure, when it is determined that relevant known functions which are obvious to those skilled in the art may unnecessarily obscure the essence of the present disclosure, its detailed description is omitted.

Micropatterning Apparatus

Figure 1:
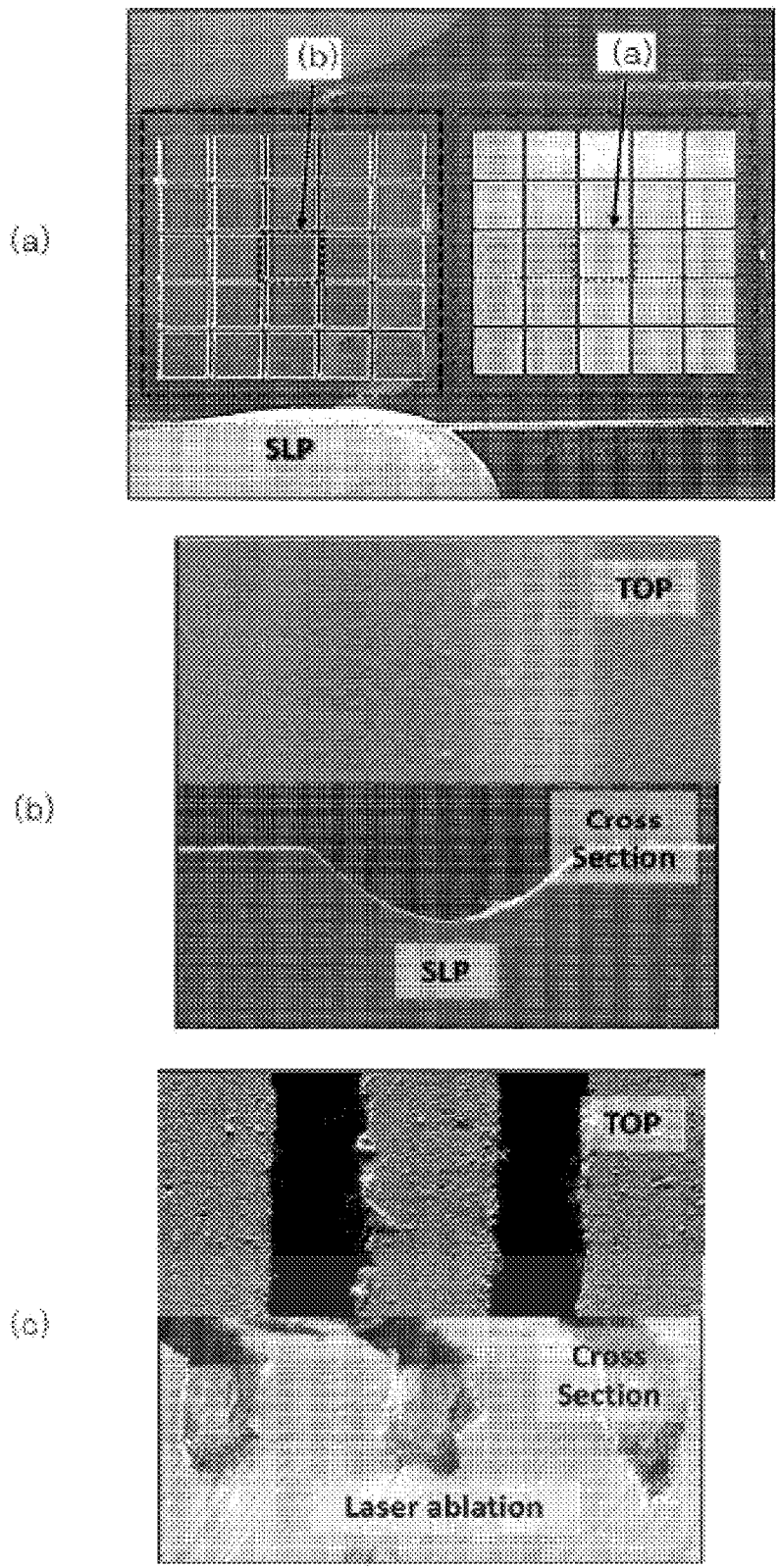
FIG. 1 is a photographic image showing a micro-device surface processed using pulsed laser according to the related art.
Figure 2:
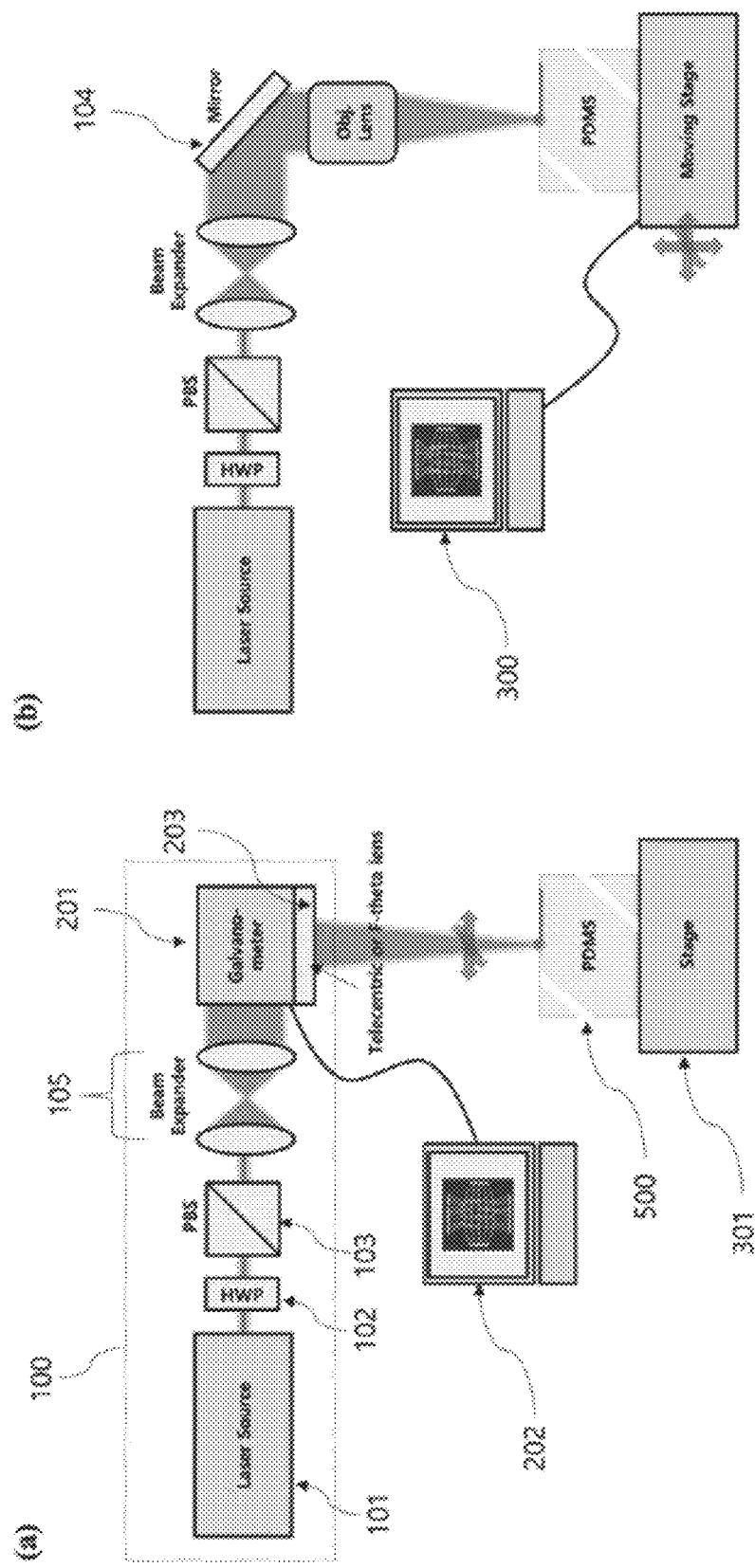
FIG. 2 is a schematic configuration diagram of a micropatterning apparatus of the present disclosure for forming micropatterns on silicone-based elastomer by laser beam irradiation.
Figure 3:
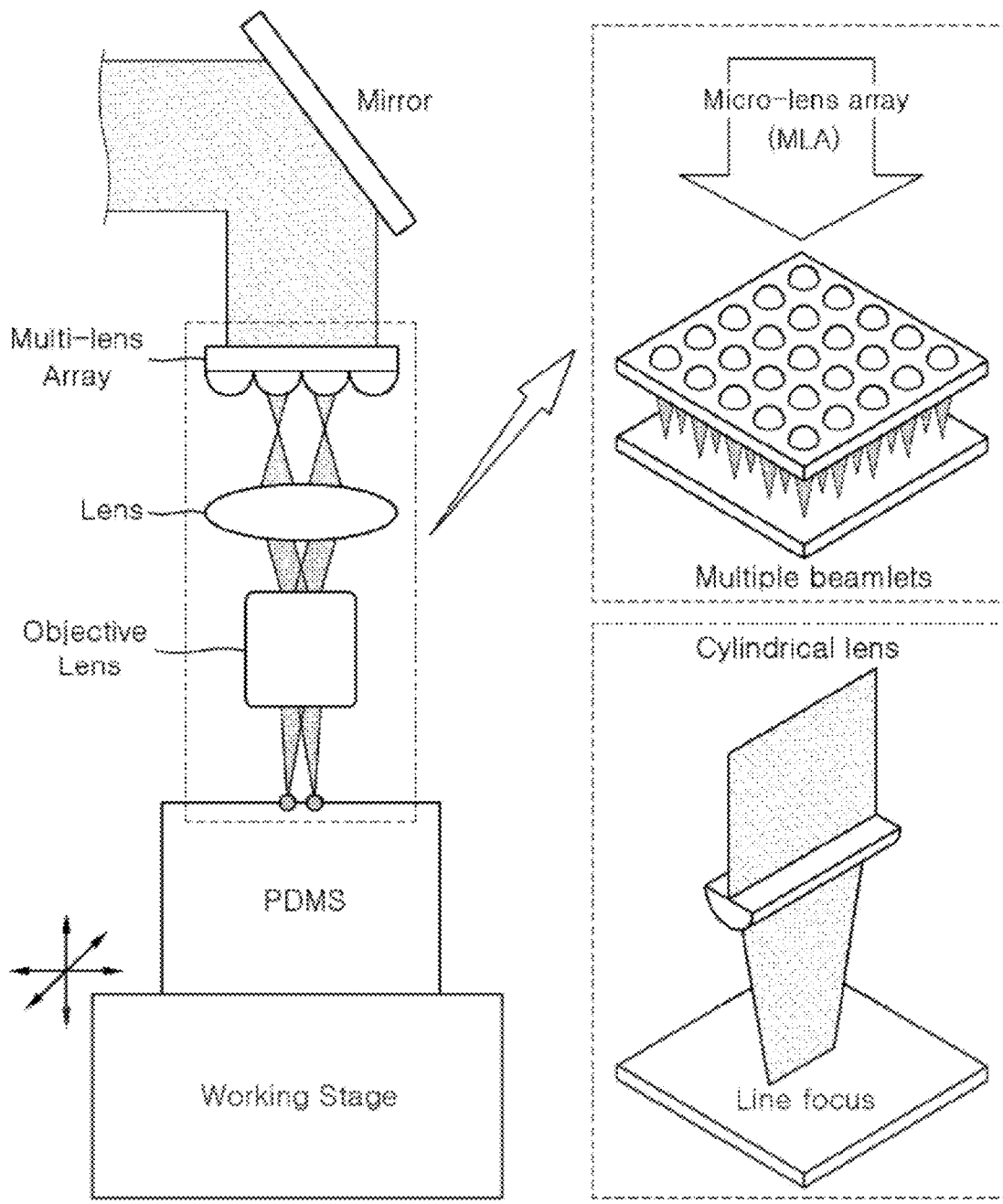
FIG. 3 is a schematic configuration diagram of another example of a micropatterning apparatus of the present disclosure for forming micropatterns on silicone-based elastomer by laser beam irradiation.
Figure 4:
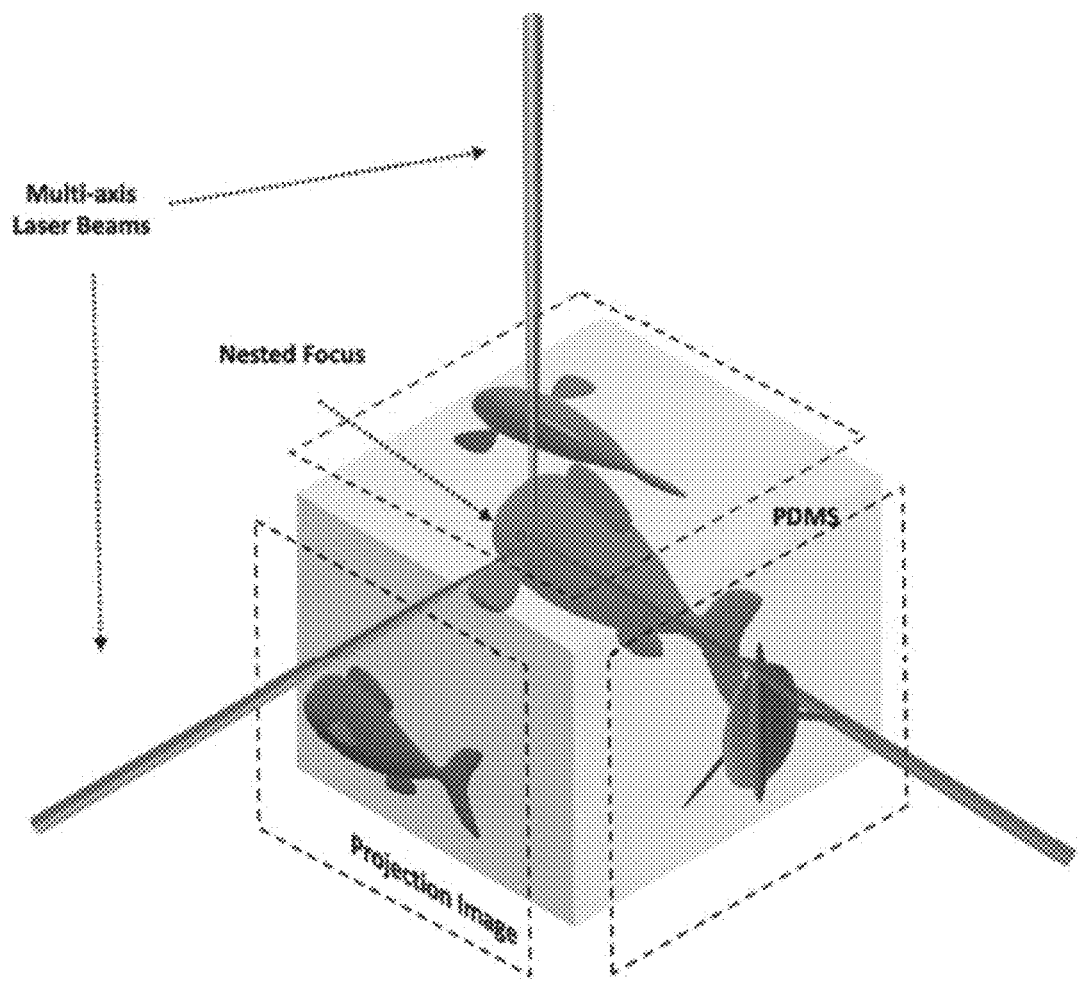
FIG. 4 is a schematic reference diagram of still another example of a micropatterning apparatus of the present disclosure for forming 3-dimensional micropatterns on silicone-based elastomer by laser beam irradiation.

FIG. 2 is a schematic configuration diagram of a micropatterning apparatus of the present disclosure for forming micropatterns on silicone-based elastomer by laser beam irradiation, FIG. 3 is a schematic configuration diagram of another example of the micropatterning apparatus of the present disclosure for forming micropatterns on silicone-based elastomer by laser beam irradiation, and FIG. 4 is a schematic reference diagram of still another example of the micropatterning apparatus of the present disclosure for forming 3-dimensional (3D) micropatterns on silicone-based elastomer by laser beam irradiation.

The micropatterning apparatus of the present disclosure will be described first with reference to FIGS. 2 to 4.

To begin with, referring to (a) of FIG. 2, the micropatterning apparatus of the present disclosure includes a laser beam generation unit 100, a stage 301 and a control unit. Meanwhile, the laser beam generation unit 100 may include a laser oscillator 101 to generate a laser beam, a waveplate 102, a polarized beam splitter (PBS) 103, a mirror 104, a beam expander 105 and a laser beam scanner 201, but the present disclosure is not limited thereto. The laser beam scanner 201 may include a galvanometer scanner.

The laser oscillator 101 includes an optical amplifier and an optical resonator, and outputs a continuous-wave laser or a pulse laser. In the case of pulse laser, ultrashort pulse laser may be preferably used.

The waveplate 102 is a module for delivering the laser beam without attenuation, path deviation or position change and controlling the polarization direction. The waveplate may include a Half Wave Plate (HWP) or a Quarter Wave Plate (QWP), but the present disclosure is not limited thereto. The polarized beam splitter 103 is configured to provide first and second beamlets through different first and second exit surfaces respectively from the laser beam incident on the incident surface. The power of the laser may be controlled at the laser source, but for the stable operation of the source, the power of the laser beam may be controlled using the waveplate and the polarized beam splitter. That is, the laser emitted from the laser source is polarized at a specific angle while passing through the waveplate, and then is split into two beamlets while passing through the polarized beam splitter. In this instance, the intensity ratio of the two beamlets may be adjusted according to the polarization angle, and the power of the beamlet to use may be precisely controlled in this way.

The mirror 104 is a module for expanding the incident beam on the beam expander 105 more than the output to change the direction of the laser beam. However, the mirror may be omitted in case that the laser source is directly connected or a fiber laser is used.

The beam expander 105 may be used together in case that a galvanometer scanner is used, and otherwise, may be omitted.

In the present disclosure, a galvanometer scanner may be used for the laser beam scanner 201. The galvanometer scanner may be used for manipulation requiring fast scanning, and includes a driving motor to move the galvanometer scanner in x, y and z-axis directions and a lens module with a lens mounted on bottom. In this instance, the lens may include a telecentric lens or an F-theta lens. However, the present disclosure is not limited thereto, and various types of lenses such as a multi-lens array or a cylindrical lens shown in FIG. 3 may be used.

A laser beam scanner control unit 202 controls the operation of the laser beam scanner which emits the laser beam output from the laser oscillator to a target to process the target. The laser beam scanner control unit 202 may be connected to the laser beam scanner to enable bi-directional communication by wired or wireless communication means, and a patterning operation may be automatically performed according to a pre-made patterning program using a general-purpose external terminal including a computer, a laptop, a network-attached storage and a mobile device (for example, a tablet device, a smartphone), or an operator may perform the patterning operation through the terminal.

Meanwhile, as shown in (b) of FIG. 2, instead of the galvanometer scanner, the laser beam scanner including a common objective lens may be used for more precise processing. In this case, more preferably, the stage rather than the scanner may be moved (in the x-axis, y-axis, or z-axis). In this case, a stage control unit 300 controls a driving device to move the stage in the x-axis, y-axis, or z-axis.

The target 500 for forming micropatterns is placed on the stage 301. In the present disclosure, silicone-based elastomer may be used for the target. In particular, initiator-loaded silicone-based elastomer is used for the target.

Referring to FIG. 4, when 3D scanning with high precision is necessary, the laser beam generation unit of the micropatterning apparatus includes a first laser beam generation unit to generate a first axis laser beam, a second laser beam generation unit to generate a second axis laser beam, and a third laser beam generation unit to generate a third axis laser beam. The first to third laser beam generation units are configured to have an intersection point where the first axis laser beam, the second axis laser beam and the third axis laser beam intersect at a point. In case that a single laser beam generation unit is used, forming 3D micropatterns (for forming 3D structures) is not impossible, but there are many limitations due to the direction of incidence of the fixed laser beam. However, as shown in FIG. 4, when the intersection point is formed using the plurality of laser beam generation units, it is possible to freely form 3D micropatterns, thereby easily forming 3D structures of various shapes.

Hereinafter, a method for micropatterning on silicone-based elastomer using the above-described micropatterning apparatus of the present disclosure will be described.

Micropatterning Method

Figure 6:
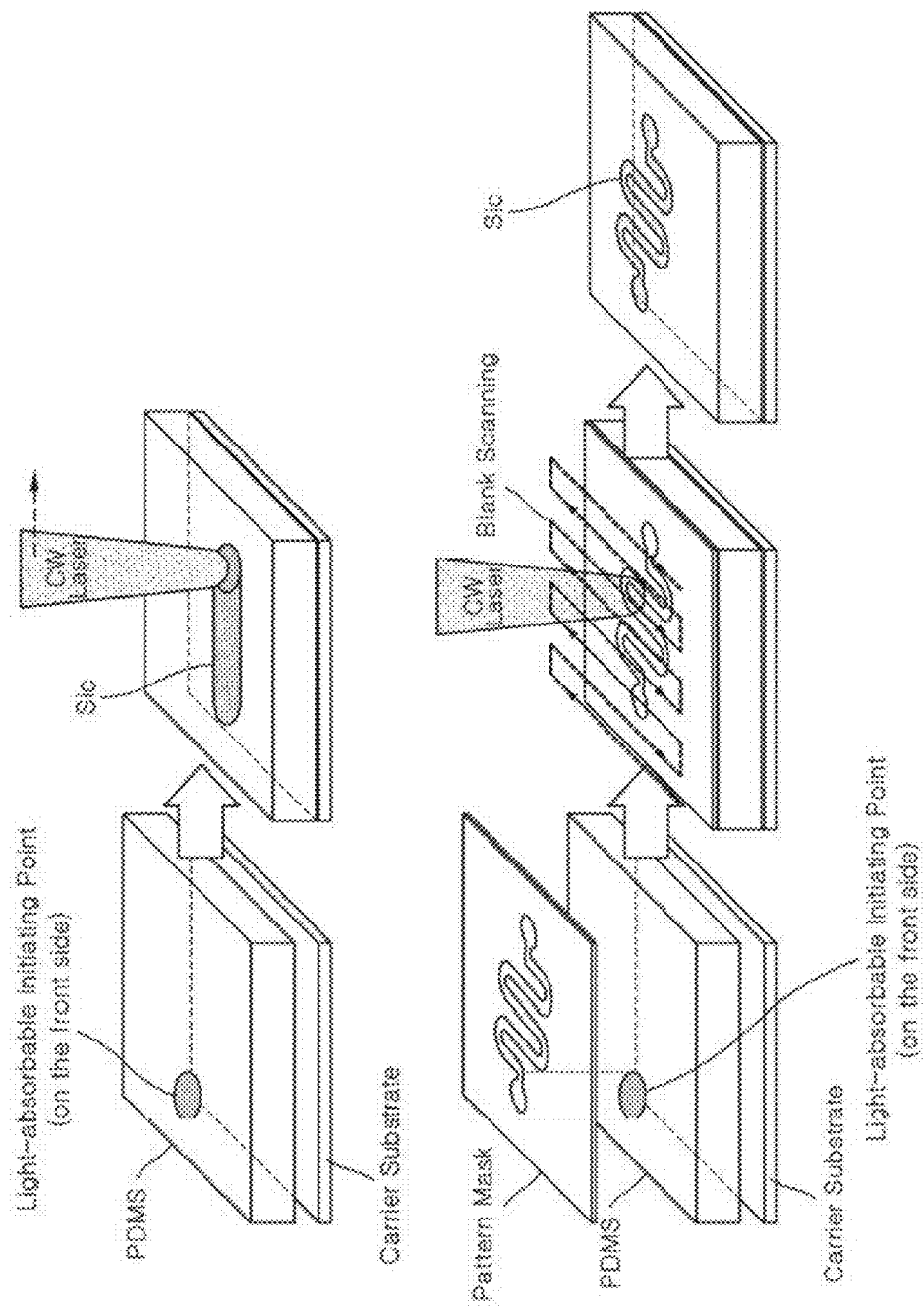
FIG. 6 is a reference diagram of various examples in which an initiator is formed on a surface of a polydimethylsiloxane (PDMS) slab on which a laser beam is incident and micropattern is formed through chain pyrolysis according to a micropatterning method of the present disclosure.
Figure 7:
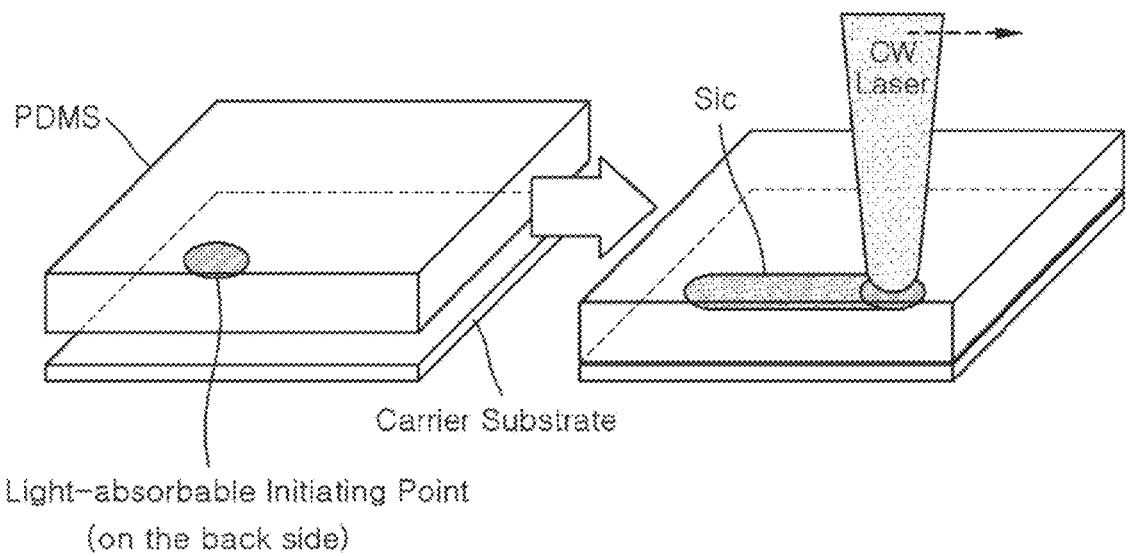
FIG. 7 is a reference diagram of various examples in which an initiator is formed on a surface opposite to a surface of a PDMS slab on which a laser beam is incident and micropattern is formed through chain pyrolysis according to a micropatterning method of the present disclosure.

FIG. 5 is a schematic diagram of a process of forming micropattern on silicon-based elastomer through chain pyrolysis according to the micropatterning method of the present disclosure, FIG. 6 is a reference diagram of various examples in which an initiator is formed on a surface of a polydimethylsiloxane (PDMS) slab on which a laser beam is incident and micropattern is formed through chain pyrolysis according to the micropatterning method of the present disclosure, and FIG. 7 is a reference diagram of various examples in which an initiator is formed on a surface opposite to a surface of a PDMS slab on which a laser beam is incident and micropattern is formed through chain pyrolysis according to the micropatterning method of the present disclosure.

The micropatterning method of the present disclosure starts with forming the initiator at a position of the silicone-based elastomer. A target of the micropatterning method of the present disclosure is silicone-based elastomer having high optical transmittance and transparency, and the silicone-based elastomer having high optical transmittance and transparency allows a laser beam to pass therethrough and thus cannot induce pyrolysis. The initiator is able to absorb light and serves to generate high-temperature heat by the laser beam.

A typical example of the silicone-based elastomer includes PDMS or ecoflex® (BASF). However, the present disclosure is not limited thereto, and other silicone-based elastomers may be applied.

The area in which the initiator is formed is referred to as a first area 1. The initiator may be formed at any position of the silicone-based elastomer, and the initiator may be disposed on the surface of the silicone-based elastomer, or may be inserted or embedded in the silicone-based elastomer.

The initiator may include a light-absorbing color pigment, dye, ink or a solution or a solid including at least one of them. However, the present disclosure is not limited thereto, and the initiator may include any type of initiator that is able to absorb a laser with a higher light absorption rate than the light absorption rate of the silicone-based elastomer itself.

Subsequently, first pyrolysis is induced in the first area 1 by laser beam irradiation to the initiator using the micropatterning apparatus which emits the laser beam. The silicone-based elastomer of the first area 1 develops SiC or trace amounts of SiOC, $SiO_2$, nonstoichimetric silica by the first pyrolysis. In this instance, Localized Heated Zone (LHZ) is formed near the first area 1 by heat transfer, and may be referred to as a second area 2. The second area 2 does not have the initiator, but becomes able to absorb light since second pyrolysis occurs by the heat transfer.

When the laser beam moves to the second area 2, light absorption occurs in the second area 2. Heat generated by the light absorption is transferred to the proximity of the second area 2 to form a new LHZ near the second area 2. That is, another new second area 2 in which light can be absorb is formed near the second area 2, in which light can be absorbed, formed near the first area 1. That is, chain pyrolysis is induced with the movement of the laser beam.

Accordingly, the micropatterning apparatus of the present disclosure may be used in the micropatterning on the silicone-based elastomer by using the laser beam like a pen or a brush. For example, the micropatterning apparatus of the present disclosure may form micropatterns very efficiently and quickly by using the laser beam like one touch drawing using a writing instrument.

Additionally, it is possible to form micropatterns having height differences by repeating scans on the area scanned by the laser beam or varying the scanning duration of specific positions. More specifically, it is possible to achieve gray-scale lithography technology that forms various aspect-ratio structures with only one patterning process by controlling the laser intensity or the scanning speed for each position or using repeated scanning.

FIG. 6 schematically shows the micropatterning method in case that the initiator is formed on the incident surface of the silicone-based elastomer. The silicone-based elastomer has a first surface on which the laser beam is incident, and a second surface opposite the first surface. FIG. 6 at (a) and (b)shows an example in which the initiator is formed on the first surface.

Referring to (a) of FIG. 6, a micropattern is formed using first pyrolysis induced by laser beam irradiation to the initiator and its subsequent second pyrolysis. The micropattern is formed along the path of the laser beam.

In contrast, in (b) of FIG. 6, a mask having a hole corresponding to the micropattern is used. The initiator is formed on the first surface of the silicone-based elastomer, and at the same time, the mask is positioned. Additionally, the laser beam scans blank. The laser beam does not move according to the micropattern, and the laser beam scans the front surface from left to right. Since the mask has the hole corresponding to the micropattern, a micropattern is formed starting from the position of the hole at which the initiator is disposed during blank scanning.

FIG. 7 schematically shows the micropatterning method in case that the initiator is formed on the opposite surface to the incident surface of the silicone-based elastomer. That is, it is an example in which the initiator is formed on the second surface on the basis of (a) and (b) of FIG. 6.

As shown in FIG. 7, in case that the initiator is formed on the opposite surface to the incident surface of the silicone-based elastomer, it can be preferably used to form 3D structures.

In case that the initiator is formed on the incident surface of the silicone-based elastomer, when pyrolysis products are formed by pyrolysis, the pyrolysis products disallow the laser to pass through, so it is not easy to induce pyrolysis in the depth-wise direction.

However, when the initiator is formed on the opposite surface to the incident surface of the silicone-based elastomer, even though SiC is formed by pyrolysis, the laser beam can pass through silicone-based elastomer without interference. For example, a conical micropattern may be formed by forming a circular pyrolysis area over a wide area by laser beam irradiation to the initiator of the opposite surface and then repeatedly drawing circles thereon with a gradual decrease in area multiple times.

Referring to FIG. 7, the micropattern is formed using first pyrolysis induced by laser beam irradiation to the initiator and its subsequent second pyrolysis. The micropattern is formed along the path of the laser beam. As opposed to (a) of FIG. 6, the laser beam passes through the silicone-based elastomer and thermally decomposes the opposite surface on the path of the laser beam.

Figure 8:
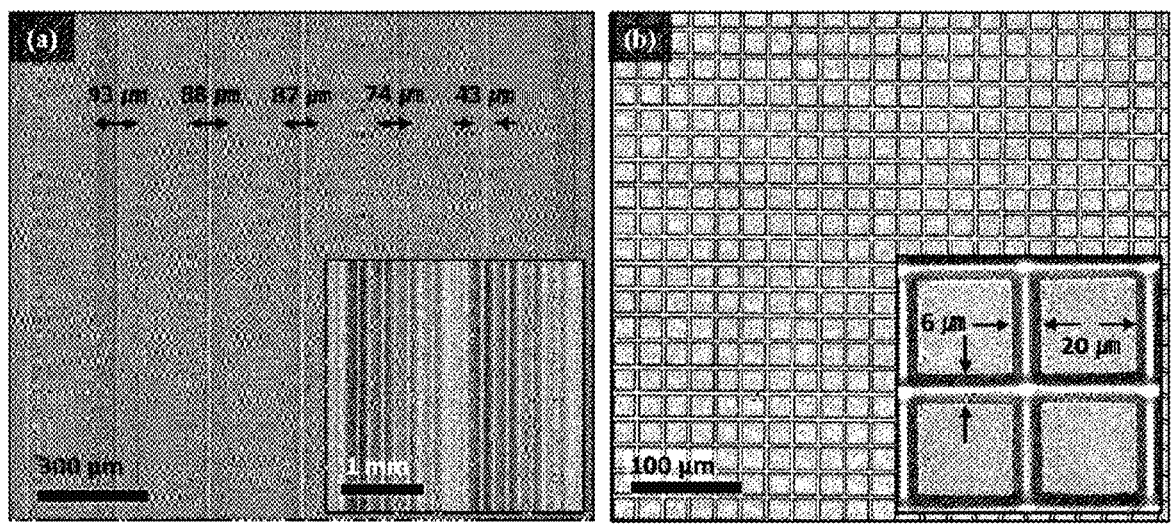
Figure 10:
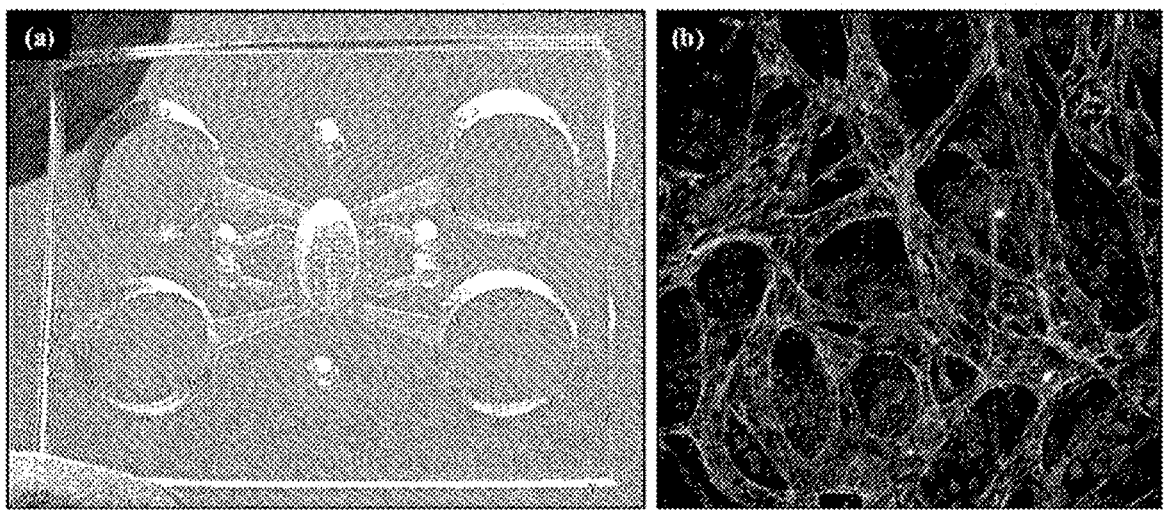
FIG. 10 is a photographic image showing a PDMS micropatterned chip on which micropatterns are formed using chain pyrolysis induced by laser beam irradiation according to a micropatterning method of the present disclosure and blood vessel cells cultured in vitro using the same.

FIGS. 8 and 9 are magnified photographic images of a micropatterned chip fabricated according to the micropatterning method of the present disclosure in various embodiments of the present disclosure, and FIG. 10 is a photographic image showing a PDMS micropatterned chip on which micropatterns are formed using chain pyrolysis induced by laser beam irradiation according to the micropatterning method of the present disclosure and blood vessel cells cultured in vitro using the same. In particular, FIG. 10 shows blood vessels stably formed by blood vessel cell culture in the micropatterned chip fabricated according to the method of the present disclosure.

These various embodiments of the present disclosure are provided to describe the present disclosure, and the present disclosure will encompass any other micropatterned chip that may be fabricated by those having ordinary skill in the technical field pertaining to the present disclosure based on the understanding of the present disclosure. Meanwhile, the unique properties of the micropatterned chip fabricated according to the micropatterning method of the present disclosure will be described in the following embodiments.

Figure 11:
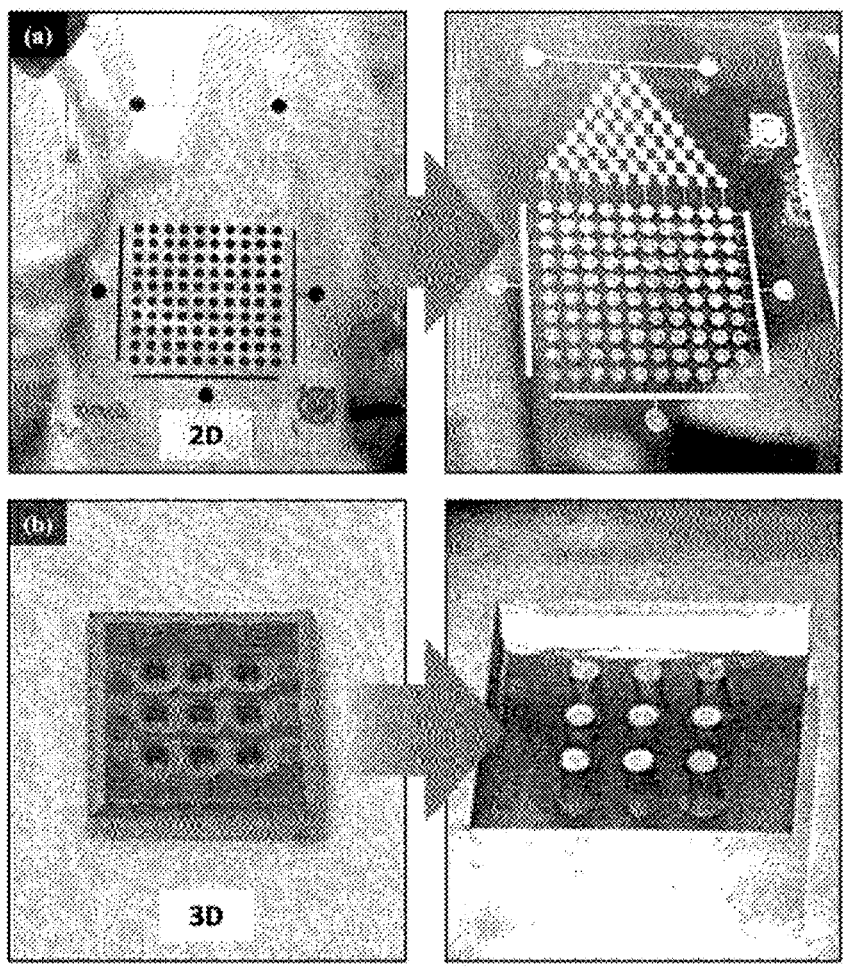
FIG. 11 at (a) shows a photographic image showing the removal by ultrasonication and FIG. 11 at (b) shows a photographic image showing the removal by a taping method or an external mechanical force, for a PDMS micropatterned chip on which micropatterns are formed using chain pyrolysis induced by laser beam irradiation according to the micropatterning method of the present disclosure.

(a) of FIG. 11 is a photographic image showing the removal by ultrasonication, and (b) of FIG. 11 is a photographic image showing the removal by a taping method or an external mechanical force, for the PDMS micropatterned chip on which micropatterns are formed using chain pyrolysis induced by laser beam irradiation according to the micropatterning method of the present disclosure, and FIG. 12 shows the X-ray diffraction (XRD) analysis results of the pyrolysis products removed by the method of FIG. 11.

When the micropatterns are formed by laser beam irradiation, pyrolysis products are generated in the area in which the micropatterns are formed. As a result of XRD analysis of the pyrolysis products, it is found that most of the pyrolysis products are SiC or SiOC, and trace amounts of $SiO_2$ or amorphous silica is formed.

The pyrolysis products are separated from the silicone-based elastomer very easily. The pyrolysis products are detached only by slightly bending the silicone-based elastomer.

However, to remove the pyrolysis products more clearly, the pyrolysis products may be removed from the silicone-based elastomer using an ultrasound after soaking in ethanol, or may be removed using a tape or an external force.

Figure 13:
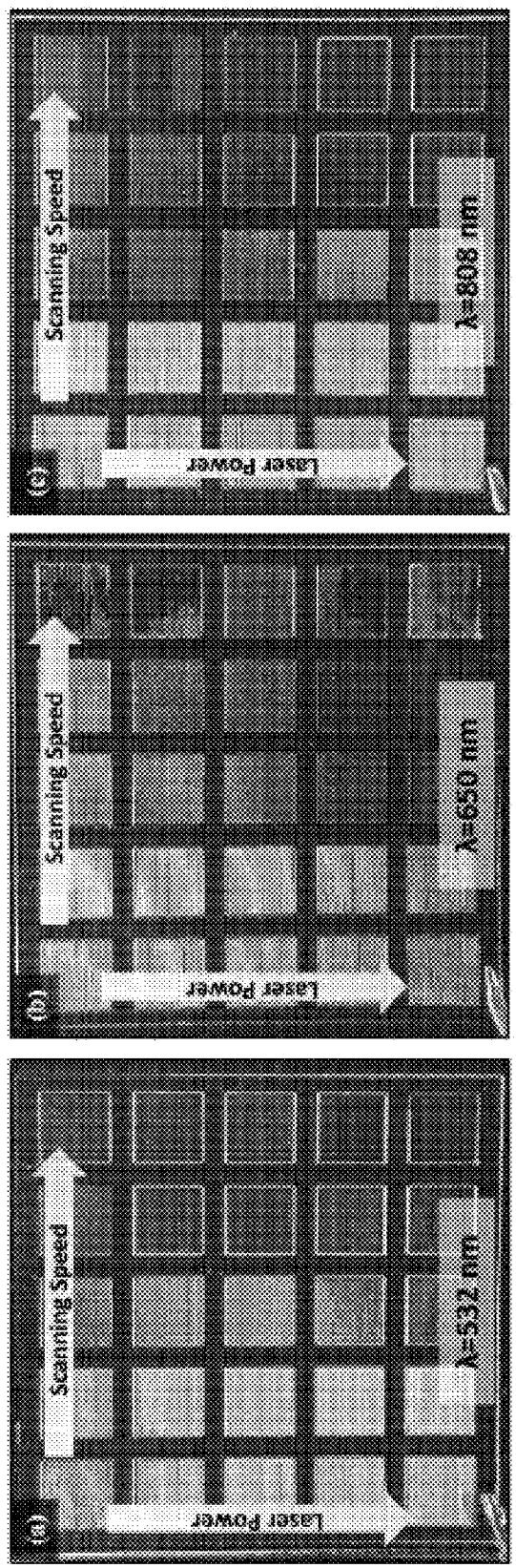
FIG. 13 shows the patterning results using laser beams of various wavelengths according to an embodiment of the present disclosure.

FIG. 13 shows the patterning results using laser beams of various wavelengths according to an embodiment of the present disclosure. In FIG. 13, laser beams of 532 nm, 650 nm and 808 nm wavelengths are used in an embodiment of the present disclosure, and it can be seen that good micropatterns are formed irrespective of the wavelength. Preferably, the wavelength of the laser beam may be 200 nm to 1,000 nm.

Figure 14:
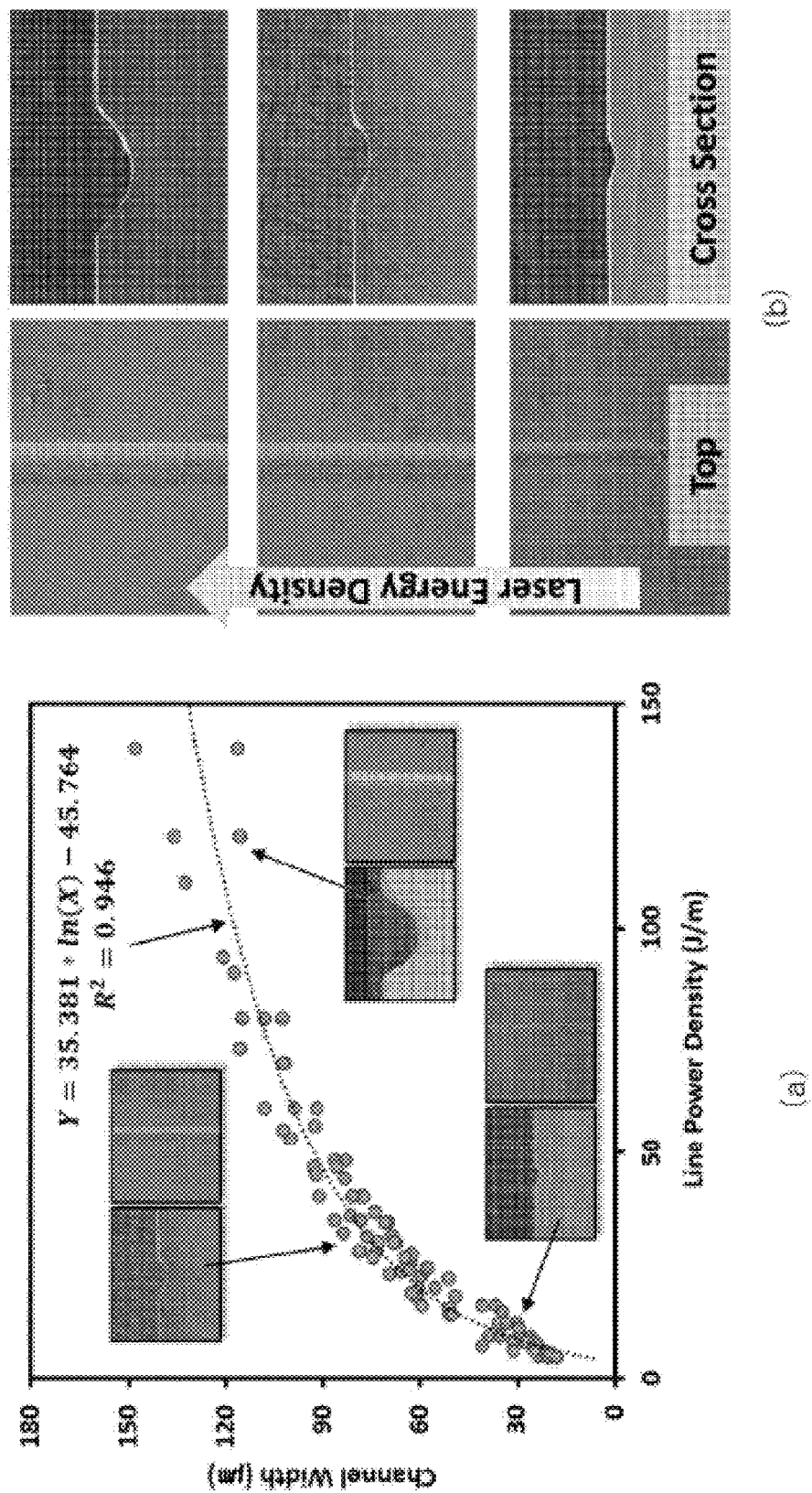
FIG. 14 is a graph showing a correlation between the scanning power of a laser beam and the channel size of micropattern formed according to the present disclosure.

FIG. 14 is a graph showing a correlation between the scanning power of the laser beam and the channel size of the micropattern formed according to the present disclosure. It can be seen from FIG. 14 that as the scanning power (J/m) of the laser beam increases, the depth and width of the microchannel increases in proportion to the scanning power of the laser beam, but the width increases at a higher speed.

FIG. 15 is a graph showing a correlation between the power density of the laser beam and the channel layer depth of the micropattern formed according to the present disclosure. Referring to FIG. 15, it is found that the layer depth of the channel formed by the laser beam increases in proportion to the power density (J/m) of the laser beam.

Figure 16:
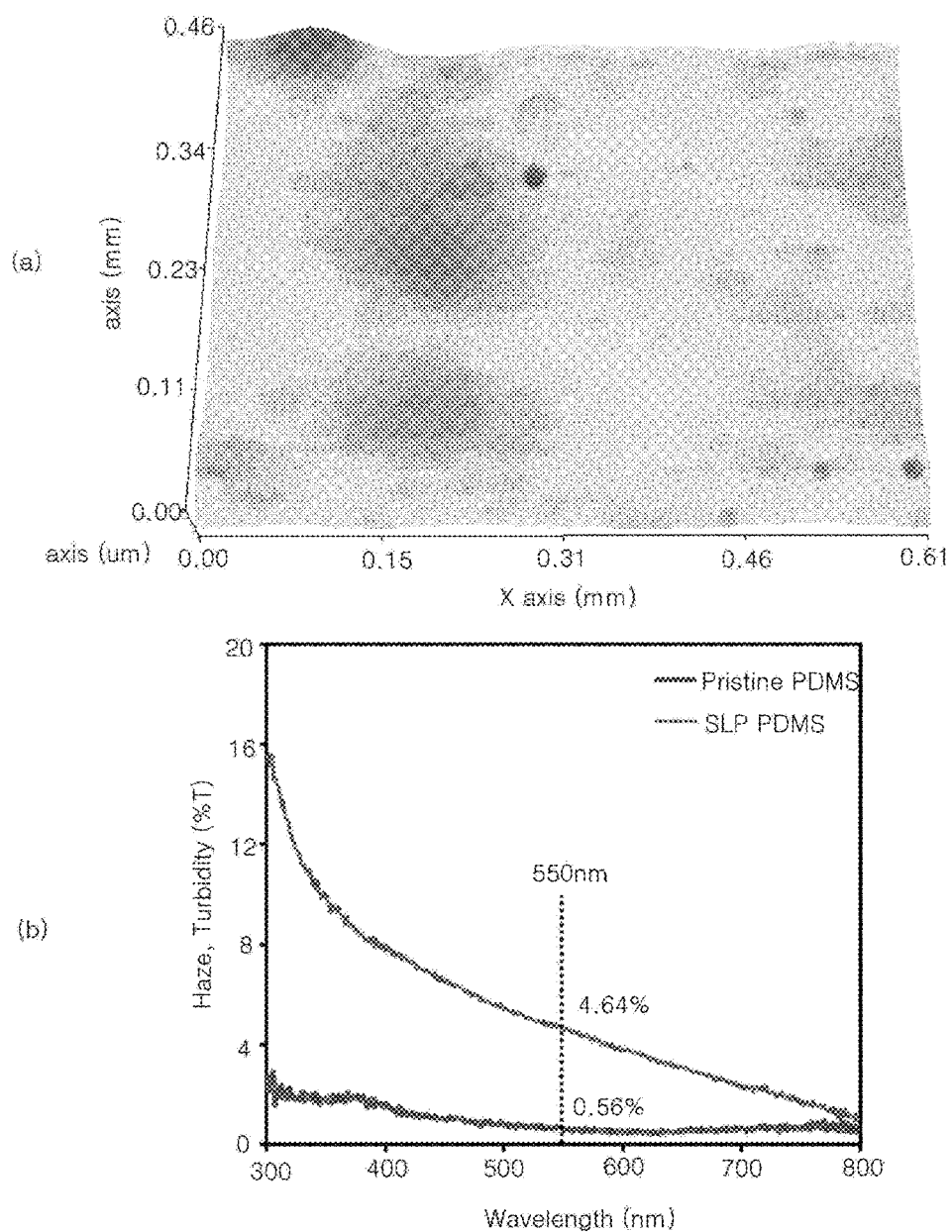
FIG. 16 shows the surface shape and turbidity measurement results of micropattern formed according to the present disclosure.

FIG. 16 shows the surface shape and turbidity measurement results of the micropattern formed according to the present disclosure. Referring to (a) of FIG. 16, it can be seen that the micropatterning method of the present disclosure inevitably forms small grooves on the micropattern surface. These grooves make the micropattern surface slightly opaque. As a result, as can be seen from (b) of FIG. 16, in the haze characteristics, pristine PDMS has turbidity of about 0.5% T, while the micropattern has turbidity of 4% T or more. The position at which the micropattern is formed has a turbidity difference by about 8 times or more compared to the pristine PDMS.

Figure 18:
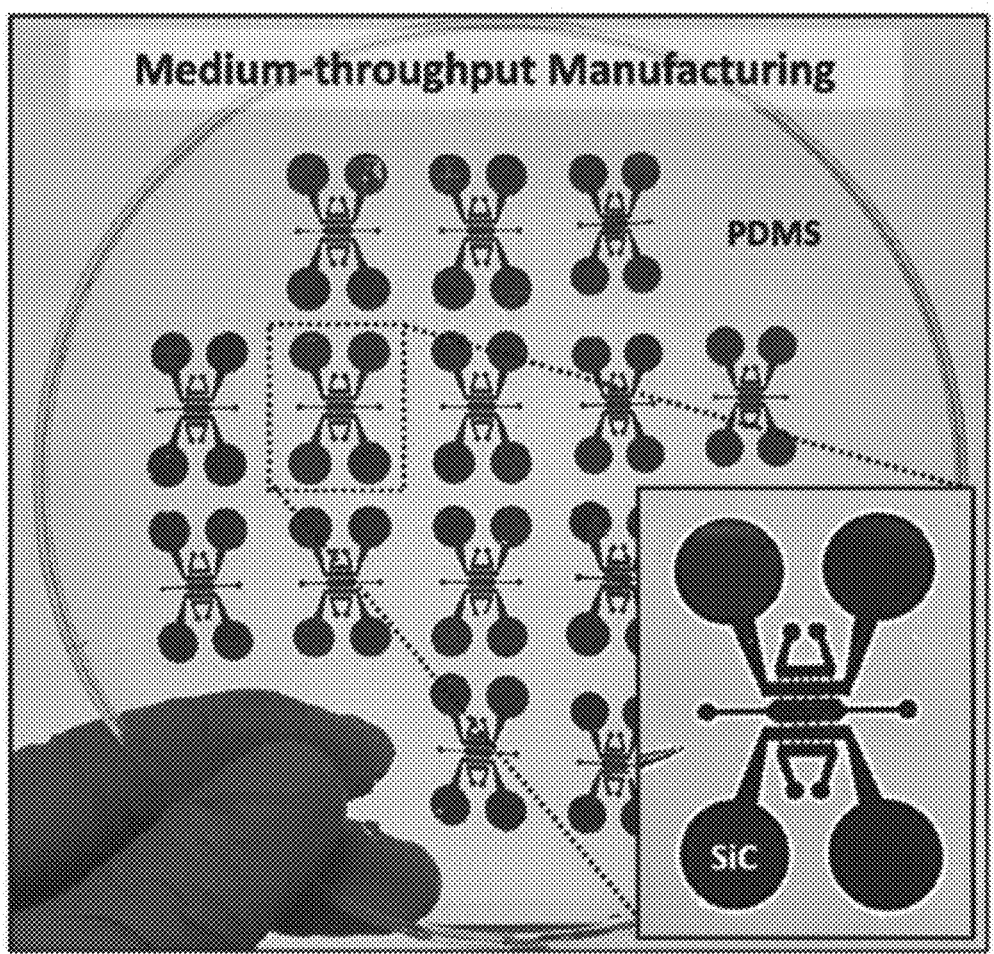
FIG. 18 shows a vessel-on-a-chip array in a micropatterned chip fabricated according to the present disclosure.

FIG. 17 shows a table of various embodiments of the micropatterned chip fabricated according to the present disclosure, and FIG. 18 shows a vessel-on-a-chip array in the micropatterned chip fabricated according to the present disclosure.

The present disclosure described hereinabove will fabricate microfluidic chips and cell culture chips shown in FIGS. 17 and 18 by the micropatterning method.

Figure 19:
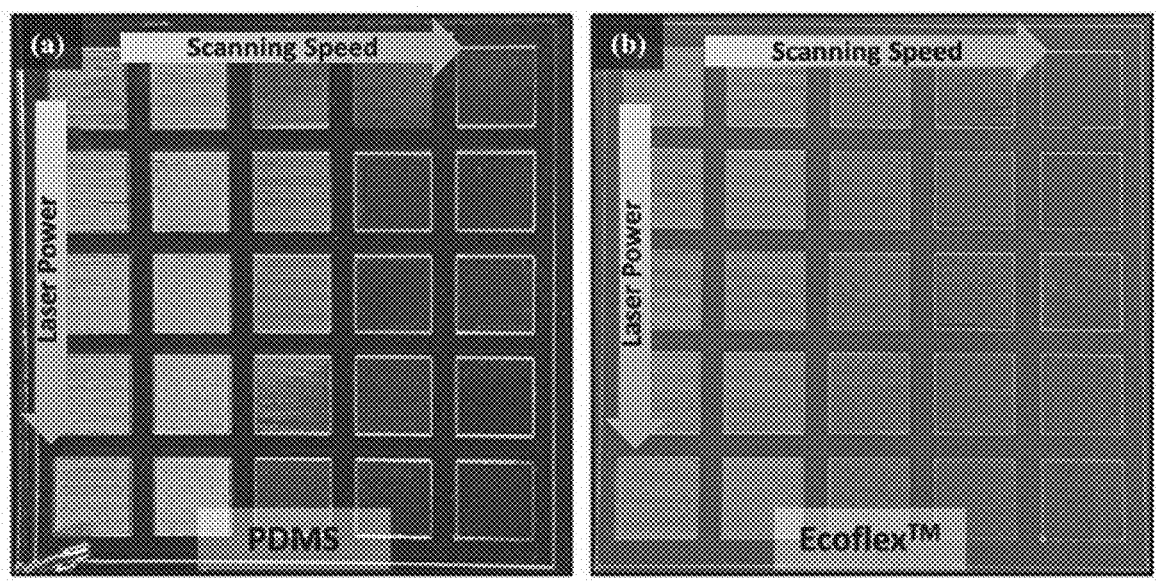
FIG. 19 at (a) shows a patterning result of PDMS and FIG. 19 at (b) shows a patterning result of ecoflex® (BASF) using chain pyrolysis induced by laser beam irradiation according to a micropatterning method of the present disclosure.
Figure 20:
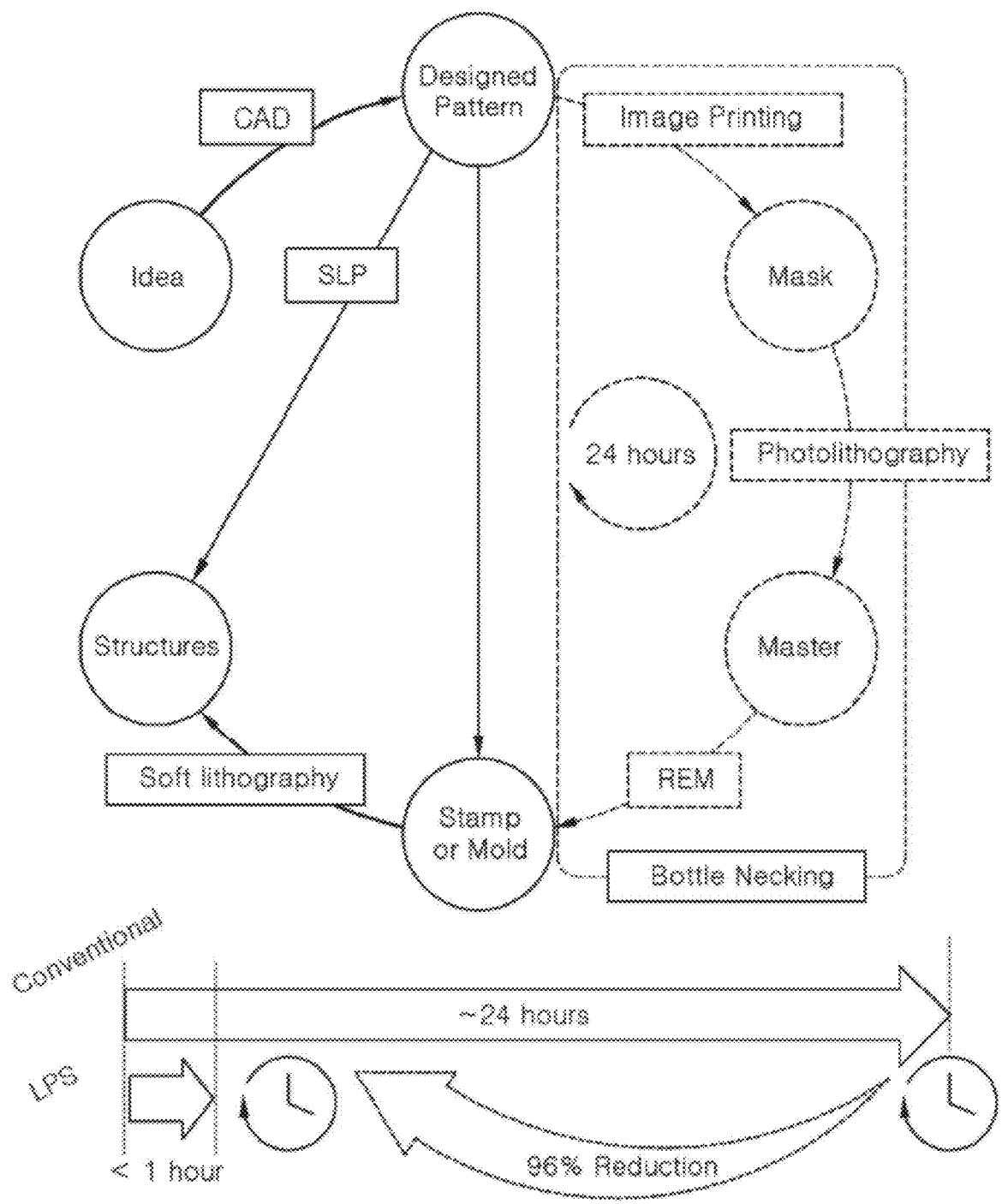
FIG. 20 schematically shows a micropatterning method (LPS) using a laser beam of the present disclosure compared with the conventional method using lithography.

FIG. 19(A) shows the patterning result of PDMS and (b) of FIG. 19 shows the patterning result of ecoflex® (BASF) using chain pyrolysis induced by laser beam irradiation according to the micropatterning method of the present disclosure. The PDMS and ecoflex® correspond to typical silicone-based elastomers. Referring to FIG. 19, it can be seen that micropatterns of high level are formed on the PDMS and ecoflex® by the micropatterning method of the present disclosure.

EXAMPLE

Example 1: Preparation of PDMS Slab

A PDMS slab is prepared by mixing resin (Dow Corning) with a curing agent (Sylgard184, Dow Corning) at a ratio of 10:1. Subsequently, degassing and curing processes are performed in a sequential order using a vacuum bell-jar and a curing oven (OF-12G, JEIO TECH) at 60° C. for 2 hours or longer.

Example 2: Construction of Micropatterning Apparatus

In this embodiment, two types of computer controlled laser beam scanning systems are used. For quick patterning, a galvanometer (hurrySCAN II, Scanlab) with a telecentric lens (f=103 mm) is used, and for micropatterning of 10 μm or less, a computer controlled 2-axis stage (ANT130-060-XY-25DU-XY-CMS-MP-PLUS, Aerotech) and a high magnification objective lens (M Plan Apo 50X, Mitutoyo) are used. For both the two, a continuous-wave laser (532 nm, Sprout-G-5W, Lighthouse Photonics) is used as a main laser source, and comparison with 650 nm and 808 nm is made.

Example 3: Fabrication of Micropatterned Chip

The cured PDMS slab prepared in the example 1 goes through surface treatment using a taping (Scotch Magic Tape, 3M) method to remove impurities such as dust from the surface. The surface-treated PDMS slab is placed on a glass used as a carrier substrate. Computer controlled laser scanning having appropriate scanning parameters in the power or scanning speed is used by a front surface scanning (FSS) method (see (a) of FIG. 6) or a back surface scanning (BSS) method (see FIG. 7). In each method, the focal point of the laser is precisely controlled for high quality processing. In FSS, the focal plane is placed on the surface of the PDMS slab on which the beam is incident. In the case of BSS, prior to the initial scanning, the focal plane of the laser is oriented toward the opposite surface to the incident surface of the PDMS slab, and subsequently, in each scanning, compensation is performed as much as the thickness of pyrolysis products newly generated by the corresponding scanning. SiC is easily removed by a taping method or an ultrasonication method. The PDMS structure may be bonded to a slide glass by the standard plasma-bonding method or may be used as a mold to fabricate a microfluidic chip.

It is found that the micropatterns of the microfluidic chip of example 3 can be formed in a very short time, and the quality of the formed micropatterns is at least equivalent to the quality of micropatterns formed using photolithography.

Accordingly, the micropatterning method of the present disclosure can easily achieve patterning on light-transmitting objects that have been impossible or inefficient to process using a laser beam by a method such as one touch drawing, and thus it is expected that the micropatterning method of the present disclosure will be widely used as a method for micropatterning on silicone-based elastomers.

The scope of protection of the present disclosure is not limited to the description and representation of the embodiments expressly described hereinabove. Additionally, it should be noted that the scope of protection of the present disclosure cannot be limited by obvious modifications or substitutions in the technical field pertaining to the present disclosure.

The invention claimed is:

1. A method for micropatterning on silicone-based elastomer, comprising:
    preparing a silicone-based elastomer;
    forming an initiator only at a first portion of the silicone-based elastomer pre-planned for the micropatterning;
    emitting a laser beam from a micropatterning apparatus which emits the laser beam to the initiator to induce first pyrolysis in the first portion, wherein second pyrolysis occurs outside of the first portion by conduction of heat generated by the first pyrolysis to form a second portion in which light can be absorbed; and
    emitting the laser beam while moving the laser beam to the second portion to form a micropattern,
    wherein pyrolysis products are SiC, SiOC, SiO$_2$, or amorphous silica,
    wherein the initiator has a lower light transmittance than the silicone-based elastomer and the pyrolysis products are generated locally in the proximity of the initiator.

2. The method for micropatterning on silicone-based elastomer according to claim 1, wherein the silicone-based elastomer has a first surface on which the laser beam is incident and a second surface opposite the first surface, and the first portion is on the first surface of the silicone-based elastomer and forms a 2-dimensional (2D) micropattern with the movement of the laser beam in a 2D area.

3. The method for micropatterning on silicone-based elastomer according to claim 1, wherein the silicone-based elastomer has a first surface on which the laser beam is incident and a second surface opposite the first surface, and the first portion is on the second surface of the silicone-based elastomer and forms a 3D micropattern with the movement of the laser beam in a 3D space.

4. The method for micropatterning on silicone-based elastomer according to claim 1, wherein the micropatterning apparatus generates a first axis laser beam, a second axis laser beam and a third axis laser beam, and the first axis laser beam, the second axis laser beam and the third axis laser beam intersect at a point to form an intersection point, and a 3D micropattern is formed with movement of the intersection point in a 3D space starting from the initiator at the first portion of the silicone-based elastomer.

5. The method for micropatterning on silicone-based elastomer according to claim 1, wherein the first portion is disposed on a surface of the silicone-based elastomer or inserted or embedded in the silicone-based elastomer.

6. The method for micropatterning on silicone-based elastomer according to claim 1, wherein the initiator is disposed on a surface of the silicone-based elastomer or inserted or embedded in the silicone-based elastomer.

7. The method for micropatterning on silicone-based elastomer according to claim 1, wherein the method further comprises removing pyrolysis products after forming the micropattern.

8. The method for micropatterning on silicone-based elastomer according to claim 1, wherein the silicone-based elastomer is Polydimethylsiloxane (PDMS).

9. The method for micropatterning on silicone-based elastomer according to claim 1, wherein the laser beam is a continuous-wave laser beam or a pulse laser beam.

10. The method for micropatterning on silicone-based elastomer according to claim 1, wherein a power density of the laser beam is less than a power density for ablation of the silicone-based elastomer.

* * * * *